United States Patent
Nakahata et al.

(10) Patent No.: US 12,275,749 B2
(45) Date of Patent: Apr. 15, 2025

(54) ROTAXANE COMPOUND

(71) Applicants: SUMITOMO RUBBER INDUSTRIES, LTD., Hyogo (JP); TOKYO INSTITUTE OF TECHNOLOGY, Tokyo (JP)

(72) Inventors: Shoko Nakahata, Hyogo (JP); Toshikazu Takata, Tokyo (JP); Toyokazu Tsutsuba, Tokyo (JP)

(73) Assignees: SUMITOMO RUBBER INDUSTRIES, LTD., Hyogo (JP); TOKYO INSTITUTE OF TECHNOLOGY, Tokyo (JP)

( * ) Notice: Subject to any disclaimer, the term of this patent is extended or adjusted under 35 U.S.C. 154(b) by 1211 days.

(21) Appl. No.: 17/049,710

(22) PCT Filed: Apr. 25, 2019

(86) PCT No.: PCT/JP2019/017761
§ 371 (c)(1),
(2) Date: Oct. 22, 2020

(87) PCT Pub. No.: WO2019/208723
PCT Pub. Date: Oct. 31, 2019

(65) Prior Publication Data
US 2021/0238205 A1    Aug. 5, 2021

(30) Foreign Application Priority Data
Apr. 26, 2018  (JP) .................................. 2018-085528

(51) Int. Cl.
| | | |
|---|---|---|
| *C07F 7/18* | (2006.01) | |
| *C08K 3/36* | (2006.01) | |
| *C08K 5/544* | (2006.01) | |
| *C08L 21/00* | (2006.01) | |

(52) U.S. Cl.
CPC .............. *C07F 7/1804* (2013.01); *C08K 3/36* (2013.01); *C08K 5/5477* (2021.01); *C08L 21/00* (2013.01)

(58) Field of Classification Search
None
See application file for complete search history.

(56) References Cited

U.S. PATENT DOCUMENTS

2022/0081493 A1*   3/2022  Akahori .................. C08C 19/22

FOREIGN PATENT DOCUMENTS

JP          2017160164 A  *  9/2017

OTHER PUBLICATIONS

A. Farcas et al., Beilstein Journal of Organic Chemistry, 1505-1514 (2012) (Year: 2012).*
H. Pines et al., 72 Journal of the American Chemical Society, 1568-1571 (1950) (Year: 1950).*
H. Sogawa et al., 42 Macromolecular Rapid Communications, 1-5 (2021) (Year: 2021).*
G. Wenz, 106 Chemical Reviews, 782-817 (2006) (Year: 2006).*
H. Dardeer et al., 7 International Journal of Chemistry, 161-167 (2015) (Year: 2015).*
K. Kellett et al., 47 Journal of Solution Chemistry, 1597-1608 (2018) (Year: 2018).*
M. Xue, 115 Chemical Reviews, 7398-7501 (2015) (Year: 2015).*
International Union of Pure and Applied Chemistry, Compendium of Chemical Terminology (IUPAC), Gold Book, pp. 19, 20, 61, 522, 778, 995, 993-994, 1479, 1503, 1538, 1594 (2014) (Year: 2014).*
C. Farber et al., 48 Chem. Commun., 227-229 (2012) (Year: 2012).*
Z. Robbins et al., 1076 Journal of Chromatography B, 117-129 (2018) (Year: 2018).*
International Union of Pure and Applied Chemistry, Glossary of Class Names of Organic Compounds and Reactive Intermediates Based on Structure (IUPAC Recommendations 1995), pp. 1307-13101995 (Year: 1995).*
G. Gokel et al., 104 Chemistry Reviews, 2723-2750 (2004) (Year: 2004).*
G. Gokel, Crown Ethers & Cryptands, p. 14 (The Royal Society of Chemistry, 1991) (Year: 1991).*
P Wang et al., 7 Polymer Chemistry, 3664-3668 (2016) (Year: 2016).*
G. Yu et al., 43 Chemistry Letters, 953-955 (2014) (Year: 2014).*
ISR for PCT/JP2019/017761, dated Jul. 16, 2019.
IPRP for PCT/JP2019/017761, dated Apr. 25, 2019 (w/ translation).
Farcas, A. et al., "Synthesis, Photophysical, and Morphological Properties of Azomethine-Persylilated a-Cyclodextrin Main-Chain Polyrotaxane", Macromolecular Chemistry and Physics, vol. 216, 2015, pp. 662-670.
Farcas, A. et al., "Synthesis and characterization of low-molecular-weight n-conjugated polymers covered by persilylated B-cyclodextrin", Beilstein Journal of Organic Chemistry, 2012, pp. 1505-1514.
Vincent, S. P. et al., "Biologically Active Hetero-glycoclusters Constructed on a Pillar [5] arene-Containing [2] Rotaxane Scaffold", Chemistry-A European Journal, vol. 22, 2016, pp. 88-92.
Sugiyama, J. et al., "Novel approach to stabilize unstable molecular wires by simultaneous rotaxane formation-synthesis of inclusion complexes of oligocarbynes with cyclic host molecules", European Journal of Organic Chemistry, 2007, pp. 4651-4653.

(Continued)

*Primary Examiner* — Alexander R Pagano
(74) *Attorney, Agent, or Firm* — Greenblum & Bernstein, P.L.C.

(57) ABSTRACT

A rotaxane compound comprising one or more cyclic molecules and an axial molecule penetrating through inner holes of the cyclic molecules and having cap structures disposed lest the cyclic molecules should be detached, where one of the cyclic molecule and the axial molecule has one of a functional group being capable of reacting with silica and a functional group being capable of reacting with a carbon-carbon unsaturated bond, and the other of the cyclic molecule and the axial molecule has the other of the functional group being capable of reacting with silica and the functional group being capable of reacting with a carbon-carbon unsaturated bond.

6 Claims, No Drawings

(56) References Cited

OTHER PUBLICATIONS

Sasabe, H. et al., "Synthesis of poly [2] rotaxane by Sonogashire polycondensation", Journal of Polymer Science, Part A: Polymer Chemistry, vol. 45, 2007, pp. 4154-4160.

Akae, Y. et al., "Cyclodextrin-Based [3] Rotaxane-Crosslinked Fluorescent Polymer: Synthesis and De-Crosslinking Using Size Complementarity, Angewandte Chemie", International Edition, vol. 57, Sep. 21, 2018, pp. 14832-14836.

Farcas, A. et al., "Effect of permodified f3-cyclodextrin on the photophysical properties of poly [2, 7- (9, 9-dioctylfluorene) - alt - (5, 5' - bithiophene)] main chain polyrotaxanes", Journal of Polymer Science, Part A: Polymer Chemistry, vol. 52, 2014, pp. 460-471.

Marois, J. et al., "Synthesis and Surface Self-Assembly of [3] Rotaxane-Porphyrin Conjugates: Toward the Development of a Supramolecular Surface Tweezer for C60", Langmuir, vol. 24, 2008, pp. 10865-10873.

Gong, X. et al., "Synthesis, characterization and in vitro evaluation of a series of novel polyrotaxane-based delivery system for artesunate", Carbohydrate Research, vol. 412, 2015, pp. 7-14.

Marois, J. et al., "[3] Rotaxane-Porphyrin Conjugate as a Novel Supramolesular Host for Fullerenes", Organic Letters, vol. 10, 2008, pp. 33-36.

Jung, S. et al., "Anti-AIDS active polyrotaxane-AZT conjugates with bioactive bulky stoppers and their nanoparticles", Journal of Polymer Science, Part A: Polymer Chemistry, vol. 50, 2012, pp. 4895-4901.

Hyun, H. et al., "Mono-, di-, or triazidated cyclodextrin-based polyrotaxanes for facile and efficient functionalization via click chemistry", Macromolecular Rapid Communications, vol. 32, 2011, pp. 326-331.

Okumura, Y. et al., "The Polyrotaxane Gel: A Topological Gel by Figure-of-Eight Cross-links", Advanced Materials, vol. 13, 2001, pp. 485-487.

Ito, K., "Novel Cross-Linking Concept of Polymer Network: Synthesis, Structure, and Properties of Slide-Ring Gels with Freely Movable Junctions", Polymer Journal, vol. 39, 2007, pp. 489-499.

Koyama, Y. et al., "Synthesis of topologically crosslinked polymers with rotaxane-crosslinking point", Polymer Journal, 2014, pp. 315-322.

EESR for EP App. No. 19791854.3, dated Jan. 31, 2022.

Aoki et al., "Mechanically Linked Block/Graft Copolymers: Effective Synthesis via Functional Macromolecular [2]Rotaxanes," ACS Macro Lett., 3:324-328 (2014).

* cited by examiner

ROTAXANE COMPOUND

TECHNICAL FIELD

The present invention relates to a rotaxane compound having reactive groups and functioning as a silane coupling agent.

BACKGROUND OF THE INVENTION

A silane coupling agent is a general term of chemicals having, in its molecule, both of a functional group reacting with and coupling with an organic material and a functional group reacting with and coupling with an inorganic material, and a purpose thereof is to couple a polymer with a filler having no compatibility with an organic material, thereby enhancing adhesion thereof.

One functional group of a silane coupling agent reacts with silanol on a surface of the filler, thereby decreasing an interaction between the fillers by the silanol and improving dispersion, and another functional group reacts with the polymer, thereby coupling the filler with the polymer via the silane coupling agent and changing an interfacial structure of the filler. As a result, a viscosity, storage elasticity, loss tangent, etc. decrease and dispersion, a mechanical strength, abrasion resistance, etc. are enhanced.

In recent years, research of a rotaxane network polymer (RCP) has been advanced enthusiastically as the key to rotaxane crosslinking. Rotaxane is a supramolecular compound having a chain molecule as an axial component and a cyclic molecule as a ring component being coupled by a spatial bonding without a covalent bond, and each of constituent elements is not subject to limitation of a bond length and a bond angle and has a high degree of freedom and mobility. Therefore, remarkable dynamic characteristics and physical properties are exhibited. The RCP is a general term of a crosslinked polymer having a rotaxane structure at a crosslinking point, and it has been reported that a high flexibility and elasticity resulting from a structure of its movable crosslinking point are exhibited (Non-Patent Documents 1-3).

PRIOR ART DOCUMENTS

Non-Patent Documents

Non-Patent Document 1: Okumura et al., Advanced Materials (2001), Vol. 13, No. 7, pp. 485-487
Non-Patent Document 2: Ito, Polymer Journal (2007), Vol. 39, No. 6, pp. 489-499
Non-Patent Document 3: Koyama, et al., Polymer Journal (2014), 46, pp. 315-322

SUMMARY OF THE INVENTION

Problem to be Solved by the Invention

However, many of RCPs are those obtained by crosslinking cyclic molecules of polyrotaxane comprising many cyclic molecules, and versatility and application thereof are limited.

If a technic for designing a functional rotaxane compound having a low molecular weight near to that of a basic unit of rotaxane and precisely controlling a property of a material having a rotaxane structure as a crosslinking point is provided, usefulness thereof is very high.

An object of the present invention is to provide a rotaxane compound functioning as a silane coupling agent.

Means to Solve the Problem

The inventors of the present invention have made intensive studies, and as a result, have found that a noble rotaxane compound, in which a functional group being capable of reacting with silica and a functional group being capable of reacting with a carbon-carbon unsaturated bond are introduced to a cyclic molecule and an axial molecule, respectively of the rotaxane compound, can be a useful silane coupling agent imparting remarkable dynamic characteristics and physical properties to a compounded composition, and have completed the present invention.

Namely, the present invention relates to:

[1] a rotaxane compound comprising one or more cyclic molecules and an axial molecule penetrating through inner holes of the cyclic molecules and having cap structures disposed lest the cyclic molecules should be detached, where one of the cyclic molecule and the axial molecule has one of a functional group being capable of reacting with silica and a functional group being capable of reacting with a carbon-carbon unsaturated bond, and the other of the cyclic molecule and the axial molecule has the other of the functional group being capable of reacting with silica and the functional group being capable of reacting with a carbon-carbon unsaturated bond,

[2] the rotaxane compound of the above [1], where the cyclic molecule is at least one selected from the group consisting of crown ether, cyclodextrin, cyclophane, calixarene, cucurbituril, and pillararene,

[3] the rotaxane compound of the above [1] or [2], where the cyclic molecule is a crown ether cyclic molecule represented by the following formula (1a), (1b) or (1c):

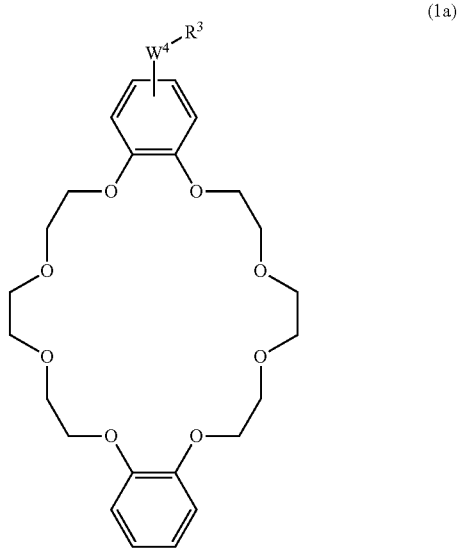

(1a)

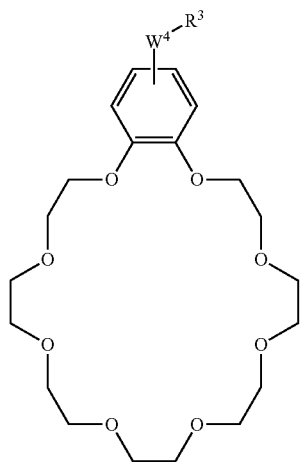

(1b)

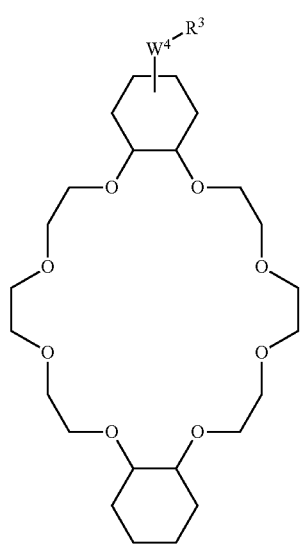

(1c)

wherein $W^4$ is a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, —$NR^1$— (where $R^1$ is an alkyl group having 1 to 6 carbon atoms), a benzene ring, a heteroaromatic ring, a saturated or partially unsaturated hydrocarbon ring and a saturated or partially unsaturated hetero ring; $R^3$ is a functional group being capable of reacting with silica or a functional group being capable of reacting with a carbon-carbon unsaturated bond; here, the cyclic molecule may be substituted with the same or different 1 to 4 groups independently selected from the group consisting of halogen, alkyl and alkoxy; and 1 to 3 of oxygen atoms constituting the ring may be replaced by NH or S, and if there are plural cyclic molecules in the rotaxane compound, the cyclic molecules may be the same or different,

[4] the rotaxane compound of any of the above [1] to [3], where the axial molecule is an axial molecule represented by the following formula (3):

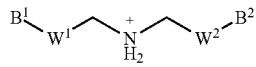

(3)

wherein $B^1$ and $B^2$ are independently cap structure; $W^1$ and $W^2$ are independently a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, —$NR^1$— (where $R^1$ is an alkyl group having 1 to 6 carbon atoms), a benzene ring, a heteroaromatic ring, a saturated or partially unsaturated hydrocarbon ring and a saturated or partially unsaturated hetero ring; here, at least either one of $B^1$ or $B^2$ is substituted with —$W^3$—$R^2$ (where $W^3$ is a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, —$NR^1$— (where $R^1$ is an alkyl group having 1 to 6 carbon atoms), a benzene ring, a heteroaromatic ring, a saturated or partially unsaturated hydrocarbon ring and a saturated or partially unsaturated hetero ring; $R^2$ is a functional group being capable of reacting with silica or a functional group being capable of reacting with a carbon-carbon unsaturated bond); $B^1$ and $B^2$ may be substituted with the same or different 1 to 4 groups independently selected from the group consisting of halogen, alkyl and alkoxy; hydrogen atoms in a secondary ammonium (—$N^+H_2$—) moiety may be substituted with alkyl, alkylcarbonyl, alkylaminocarbonyl, alkoxycarbonyl, optionally-substituted phenylcarbonyl, optionally-substituted phenylaminocabonyl, or optionally-substituted phenoxycarbonyl; when a plurality of $R^1$, $R^2$ and $W^3$ exists, those may be the same or different,

[5] the rotaxane compound of any of the above [1] to [4], where one axial molecule penetrates one of the cyclic molecules,

[6] the rotaxane compound of any of the above [1] to [5], where the functional group being capable of reacting with silica is at least one selected from the group consisting of alkoxysilyl, acetoxysilyl and chlorosilyl,

[7] the rotaxane compound of any of the above [1] to [6], where the functional group being capable of reacting with a carbon-carbon unsaturated bond is at least one selected from the group consisting of nitrile oxide, azide, nitron, nitrileimine, sydnone, methylolphenol, mercapto, sulfide, vinyl, vinylene, ethynyl, ethynylene, cyano, isocyanate, isocyanurate, epoxy, glycidyloxy, acryloyl, methacryloyl and ureido,

[8] a polymer composition comprising a polymer having a carbon-carbon unsaturated bond and the rotaxane compound of any of the above [1] to [7],

[9] the polymer composition of the above [8], where the polymer is a diene rubber,

[10] a rubber composition comprising a diene rubber, silica and the rotaxane compound of any of the above [1] to [7],

[11] a silane coupling agent comprising the rotaxane compound of any of the above [1] to [7].

Effects of the Invention

According to the present invention, a rotaxane compound that functions as a silane coupling agent is provided. Also, the present invention can realize a polymer composition comprising the rotaxane compound.

EMBODIMENT FOR CARRYING OUT THE INVENTION

Herein, unless otherwise described, interpretation such that a "compound" is in a form of a free body, salt, solvate or ion is not excluded, and such form can be construed based on a technical common knowledge. Examples of anion composing the salt include perchlorate ion, trifluoromethanesulfonate ion, hexafluorophosphate ion, trifluoroacetate ion, tetrafluoroborate ion and the like.

Herein, a "rubber" means a crude rubber which can be modified into a state of being insoluble (but being swellable) in a boiling solvent such as benzene, methyl ethyl ketone or an ethanol/toluene azeotropic mixture or an already modified elastomer material.

Herein, a "rubber compound" means a compound which is a main component composing a rubber. Examples of the rubber compound include rubber hydrocarbons such as cis-1,4-polyisoprene.

<Rotaxane Compound>

The rotaxane compound according to the embodiment of the present invention is a molecule in which a cyclic molecule and an axial molecule are bonded by a spatial bonding without a covalent bond, as per usual understanding of rotaxane by a person skilled in the art. The rotaxane compound according to the embodiment of the present invention is characterized by comprising one or more cyclic molecules and an axial molecule penetrating through inner holes of the cyclic molecules and having cap structures disposed lest the cyclic molecules should be disconnected, where one of the cyclic molecule and the axial molecule has one of a functional group being capable of reacting with silica and a functional group being capable of reacting with a carbon-carbon unsaturated bond, and the other of the cyclic molecule and the axial molecule has the other of the functional group being capable of reacting with silica and the functional group being capable of reacting with a carbon-carbon unsaturated bond. From this point of view, the rotaxane compound according to the embodiment of the present invention can be used as a novel silane coupling agent.

There is also a case where the rotaxane compound according to the embodiment of the present invention may have at least one asymmetric carbon atom. Therefore, the rotaxane compound according to the embodiment of the present invention encompasses not only its racemic modifications but also optically active substances of these compounds. Furthermore, in the case where the rotaxane compound according to the embodiment of the present invention has two or more asymmetric carbon atoms, stereoisomerism may arise. Therefore, the rotaxane compound according to the embodiment of the present invention encompasses stereoisomers of these compounds, a mixture thereof and those isolated therefrom.

There is a case where the rotaxane compound according to the embodiment of the present invention can exist as a tautomer. Therefore, the rotaxane compound according to the embodiment of the present invention also encompasses tautomers thereof.

Further, a deuterium substitute obtained by transforming any one or more of 1H of the rotaxane compound according to the embodiment of the present invention to $^2$H(D) is also encompassed in the rotaxane compound according to the embodiment of the present invention.

<Reactive Group>

The rotaxane compound according to the embodiment of the present invention has, in its structure, a functional group being capable of reacting with silica and a functional group being capable of reacting with a carbon-carbon unsaturated bond. It should be noted that herein these functional groups may be generally called simply as "reactive groups".

Examples of the functional group being capable of reacting with silica include alkoxysilyl, acetoxysilyl, chlorosilyl and the like. From the viewpoint of availability and easy handling, alkoxysilyl is preferable.

Examples of alkoxysilyl include trimethoxysilyl, triethoxysilyl, triisopropoxysilyl, dimethoxymethylsilyl, diethoxymethylsilyl, dimethylmethoxysilyl, dimethylethoxysilyl and the like.

Examples of acetoxysilyl include triacetoxysilyl, diacetoxymethylsilyl, acetoxydimethylsilyl and the like.

Examples of chlorosilyl include chlorodimethylsilyl, dichloromethylsilyl, trichlorosilyl and the like.

Examples of the functional group being capable of reacting with a carbon-carbon unsaturated bond include functional groups being capable of performing 1,3-dipole cycloaddition reaction such as nitrile oxide, azide, nitron, nitrileimine, sydnone and methylolphenol, mercapto, sulfide, vinyl, vinylene, ethynyl, ethynylene, cyano, isocyanate, isocyanurate, epoxy, glycidyloxy, acryloyl, methacryloyl, ureido and the like. Among these, nitrile oxide is suitably used in this embodiment since it is handled easily, and can perform 1,3-dipole cycloaddition reaction without a catalyst and a solvent together with not only ethynylene (carbon-carbon triple bond) but also nitrile and vinylene (carbon-carbon double bond) which are often contained in a general-purpose polymer and show a relatively inactive reactivity, and in addition, can be used in either of electron-rich and electron-deficient unsaturated bonds. It should be noted that sulfide includes polysulfides such as disulfide and tetrasulfide (hereinafter these may be collectively referred to as "(poly)sulfides)".

(Cyclic Molecules)

The rotaxane compound according to the embodiment of the present invention has, as its constituent molecules, one or more cyclic molecules. From the viewpoint of easy synthesis, a rotaxane compound having one axial molecule penetrating through 1 to 3 cyclic molecules (namely, a rotaxane compound comprising 1 to 3 cyclic molecules) is preferable. Further, a rotaxane compound having one axial molecule penetrating through one cyclic molecule (namely, [2]rotaxane), which is base units of rotaxane, is particularly preferable from the viewpoint of accurately controlling a property of a material having a rotaxane structure as a crosslinking point.

Examples of the cyclic molecules include crown ether, cyclodextrin, cyclophane, calixarene, cucurbituril, pillararene and the like. Crown ether is preferable from the viewpoint of availability, convenience and reactivity, for example, from the viewpoint that there are many cyclic molecules available on the market, a variety of structural modifications have been reported, and a given number of cyclic molecules can be encompassed in a rotaxane synthesis.

A size of a ring of the cyclic molecule is preferably 21 to 42 members, more preferably 21 to 30 members, particularly preferably 24 members.

The cyclic molecule may have one or more substituents. Examples of the substituents include alkylthio, mercapto, aminomethyl, amino, hydroxyl, hydroxymethyl, carboxyl, carboxymethyl, halogen, alkoxy, alkoxycarbonylamino (carbamate), carbamoyl, vinyl, allyl, ethynyl, formyl, acrylate, methacrylate, ether and the like. Examples of ethers include polyethers, which may have one or more substituents selected from the group consisting of phenyl and oxo, etc. The above-mentioned substituents may be directly substituted on atoms constituting the ring of the cyclic molecule, or may be connected via a spacer extending from above the atoms constituting the ring. The spacer may have one or more constituent unit selected from the group consisting of, for example, an alkylene chain, —CO—O—, —O—CO—, —O—, —CO—, —S—, —CS—, —NH—, —NR$^1$— (where R$^1$ is a substituent such as an alkyl group), an aromatic ring, a heteroaromatic ring, a saturated or partially unsaturated hydrocarbon ring and a saturated or partially unsaturated hetero ring.

It is preferable that the cyclic molecule is substituted with one or more groups represented by —W$^4$—R$^3$ (where W$^4$ is a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, —NR$^1$— (where R$^1$ is an alkyl group having 1 to 6 carbon atoms), a benzene ring, a heteroaromatic ring, a saturated or partially unsaturated hydrocarbon ring and a saturated or partially unsaturated hetero ring; R$^3$ is a functional group being capable of reacting with silica or a functional group being capable of reacting with a carbon-carbon unsaturated bond). The cyclic molecule may be substituted with the same or different 1 to 4 groups independently selected from the group consisting of halogen, alkyl and alkoxy.

Examples of the preferable cyclic molecules include 21-membered to 42-membered crown ethers which have one of the functional group being capable of reacting with silica and the functional group being capable of reacting with a carbon-carbon unsaturated bond, and yet may have one or more of the above-mentioned substituents, and 1 to 3 of oxygen atoms constituting the ring may be replaced by NH or S.

One mode of the cyclic molecule is a crown ether cyclic molecule represented by the following formula (1):

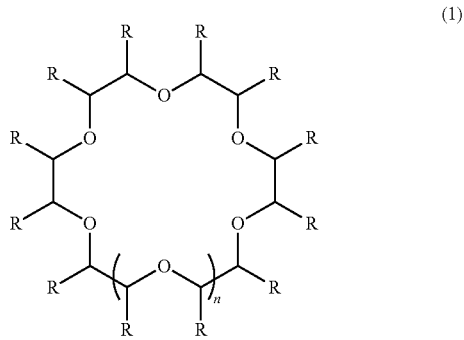

(1)

wherein each of Rs is independently a hydrogen atom, or a substituent or a reactive group which may be bonded via a spacer; "n" represents an integer of from 2 to 9 (preferably an integer of from 2 to 5); 1 to 3 of oxygen atoms constituting the ring may be replaced by NH or S; two Rs attaching to adjacent carbon atoms together with the carbon atoms bonded to the Rs may form an aromatic ring (preferably a benzene ring), a hetero aromatic ring, a saturated or partially unsaturated hydrocarbon ring or a saturated or partially unsaturated hetero ring.

Examples of the above-mentioned substituent include alkylthio, mercapto, aminomethyl, amino, hydroxyl, hydroxymethyl, carboxyl, carboxymethyl, halogen, alkoxy, alkoxycarbonylamino (carbamate), carbamoyl, vinyl, allyl, ethynyl, formyl, acrylate, methacrylate, ether and the like. Examples of the ether include polyethers having one or more substituents selected from the group consisting of phenyl and oxo, etc.

The above-mentioned spacer may have one or more constituent unit selected from the group consisting of a linear or branched alkylene chain, —CO—O—, —O—CO—, —O—, —CO—, —S—, —CS—, —NH—, —NR$^1$— (where R$^1$ is a substituent such as an alkyl group), an aromatic ring, a heteroaromatic ring, a saturated or partially unsaturated hydrocarbon ring and a saturated or partially unsaturated hetero ring.

Examples of the crown ether include dibenzo-24-crown-8,24-crown-8, benzo-24-crown-8, bis(binaphthyl)-28-crown-8, bis(biphenyl)-28-crown-8, dicyclohexyl-24-crown-8, benzo/binaphthyl-24-crown-8 and the like, each of which may have one or more substituents. Among these, dibenzo-24-crown-8,24-crown-8, benzo-24-crown-8 and dicyclohexyl-24-crown-8, each of which may have one or more substituents, are preferable, and dibenzo-24-crown-8, which may have one or more substituents, is more preferable.

The reactive groups may be directly substituted on atoms constituting the ring of the cyclic molecule, or may be bonded via the spacers extending from above the atoms constituting the ring.

More preferable mode of the cyclic molecule is the crown ether cyclic molecule represented by the following formula (1a), (1b) or (1c):

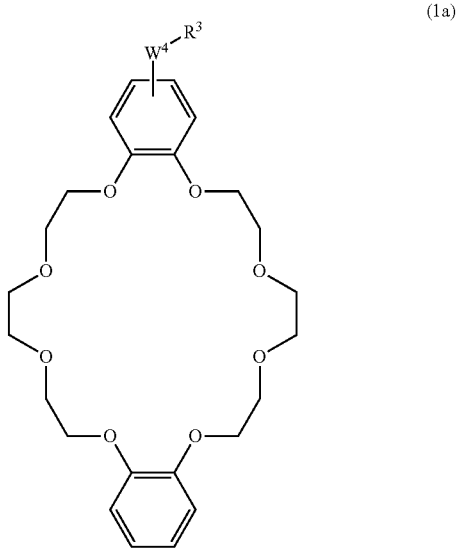

(1a)

-continued (1b)

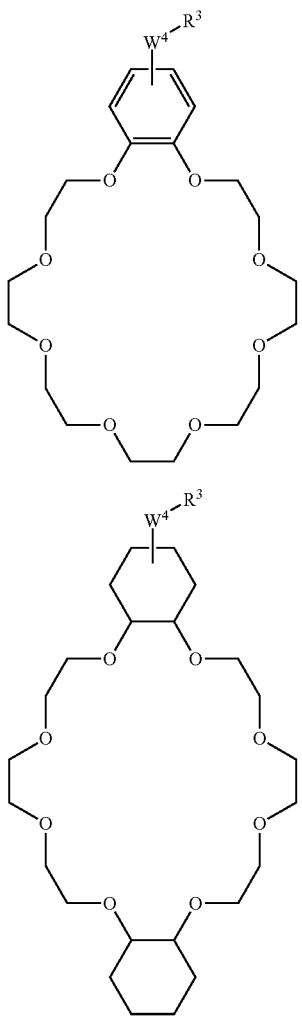

(1c)

where W⁴ is a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, —NR¹— (where R¹ is an alkyl group having 1 to 6 carbon atoms), a benzene ring, a heteroaromatic ring, a saturated or partially unsaturated hydrocarbon ring and a saturated or partially unsaturated hetero ring; R³ is a functional group being capable of reacting with silica or a functional group being capable of reacting with a carbon-carbon unsaturated bond; here, the cyclic molecule may be substituted with the same or different 1 to 4 groups independently selected from the group consisting of halogen, alkyl and alkoxy; and 1 to 3 of oxygen atoms constituting the ring may be replaced by NH or S.

W⁴ is preferably a single bond, or a spacer being composed of 1 to 100 atoms and having one or more constituent unit selected from the group consisting of linear or branched alkylene chain, —CO—O—, —O—CO—, —O—, —CO—, —S—, —NH—, a benzene ring, a 5-membered or 6-membered nitrogen-containing heteroaromatic ring, a 5-membered or 6-membered saturated or partially unsaturated hydrocarbon ring and a 5-membered or 6-membered nitrogen-containing saturated or partially unsaturated hetero ring; and more preferably a spacer being composed of 1 to 80 atoms and having one or more constituent unit selected from the group consisting of a linear alkylene chain, —CO—O—, —O—CO—, —O—, —S—, a benzene ring and a 5-membered or 6-membered nitrogen-containing saturated or partially unsaturated hetero ring.

Preferred as a group which may be substituted for the cyclic molecule are halogen, alkyl having 1 to 6 carbon atoms and alkoxy having 1 to 6 carbon atoms, and more preferred are fluorine and methyl.

Preferred as a functional group being capable of reacting with silica are alkoxysilyl, acetoxysilyl and chlorosilyl; and more preferred is alkoxysilyl.

Preferred as a functional group being capable of reacting with a carbon-carbon unsaturated bond are nitrile oxide, azide, nitron, nitrileimine, sydnone, methylolphenol, mercapto, (poly)sulfide, vinyl, vinylene, ethynyl, ethynylene, cyano, isocyanate, isocyanurate, epoxy, glycidyloxy, acryloyl, methacryloyl and ureido; more preferred are nitrile oxide, azide, mercapto, (poly)sulfide, epoxy and glycidyloxy; further preferred are nitrile oxide, mercapto and (poly)sulfide.

When there is a plurality of the above-mentioned cyclic molecules in the rotaxane compound, the cyclic molecules may be the same or different.

(Axial Molecules)

The rotaxane compound according to the embodiment of the present invention comprises the axial molecules as its constituent molecules. The axial molecules have bulky groups, namely cap structures, having an outer diameter larger than an inner diameter of the cyclic molecule. A position of the cap structures is not limited particularly as long as the axial molecules are not detached from the cyclic molecules, and the cap structures may be disposed at ends of the axial molecule or may be disposed at an intermediate portion of the axial molecule.

The cap structures are not limited particularly as long as they are the groups bulky enough to be able to prevent the axial molecules from detaching from the cyclic molecules. Each of the cap structures can be, for example, an optionally-substituted monocyclic or polycyclic aromatic group, an optionally-substituted hetero aromatic ring, an optionally-substituted saturated or partially unsaturated hydrocarbon ring, an optionally-substituted saturated or partially unsaturated hetero ring or a non-cyclic group (for example, an alkyl group) having such a group or a ring. For example, a monocyclic group having substituents can be a single ring having one or more bulky substituents like a tert-butyl group. Examples of the bulky group include phenyl which may be replaced by one or more alkyl groups having 1 to 6 carbon atoms (for example, 3,5-di-tert-butylphenyl, 3,5-dimethylphenyl, 2,6-dimethylphenyl, 3,5-dinitrophenyl, 4-tert-butylphenyl and 2,4,6-trimethylphenyl), tert-butyl, diphenylmethyl, trityl, naphthyl, anthracenyl and the like.

A chain length of a linker for coupling the cap structures in the axial molecules is not limited particularly as long as mobility of the above-mentioned rotaxane compound is not lost, and for example, a main chain thereof can be composed of 1 to 500, preferably 5 to 200, more preferably 10 to 100 atoms. The linker may have a substituent as long as mobility of the above-mentioned rotaxane compound is not lost. Examples of the substituent include alkylthio, mercapto, aminomethyl, amino, hydroxyl, hydroxymethyl, carboxyl, carboxymethyl, halogen, alkoxy, alkoxycarbonylamino (carbamate), carbamoyl, vinyl, allyl, ethynyl, formyl, acrylate, methacrylate, ether and the like. Examples of the ether include polyethers which may have one or more substituents selected from the group consisting of phenyl and oxo, etc.

Further, the linker may be composed of, for example, a polymer such as polyester, polyether, polyacrylate or polycarbonate or a polymer comprising such a polymer as mentioned above as a base component.

The linker may have one or more ammonium moieties (preferably secondary ammonium (—N$^+$H$_2$—) moiety). When preparing the rotaxane compound, the ammonium moiety can contribute to holding a positional relationship of a starting material of the axial molecule penetrating a main ring of the cyclic molecule by an electrostatic interaction between the ammonium moiety and an oxygen atom of the cyclic molecule. Further, a linker, in which one or more ammonium moieties have been converted to tertiary ammonium, amide, urea, carbamate or the like, can be raised as a preferable mode.

For example, the linker has one or more ammonium moieties, and may have one or more constituent unit selected from the group consisting of a linear or branched alkylene chain, —CO—O—, —O—CO—, —O—, —CO—, —S—, —CS—, —NH—, —NR$^1$— (where R$^1$ is a substituent such as an alkyl group), an aromatic ring, a heteroaromatic ring, a saturated or partially unsaturated hydrocarbon ring and a saturated or partially unsaturated hetero ring. Further, hydrogen atoms of the ammonium moiety may be substituted with alkyl, alkylcarbonyl, alkylaminocarbonyl, alkoxycarbonyl, optionally-substituted phenylcarbonyl, optionally-substituted phenylaminocabonyl, or optionally-substituted phenoxycarbony.

When the linker has one or more secondary ammonium moieties, the rotaxane compound may comprise counter anions (for example, perchloric acid ion, trifluoromethanesulfonic acid ion, hexafluorophosphoric acid ion, trifluoroacetic acid ion and tetrafluoroboric acid ion).

The reactive groups may be directly substituted on atoms constituting the linker or the cap structures or may be bonded via the above-mentioned spacers extending from above the atoms constituting the linker or the cap structures.

A more preferred mode of the axial molecule is an axial molecule represented by the following formula (3):

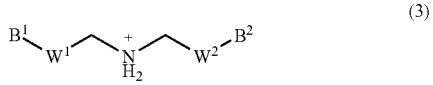

(3)

wherein B$^1$ and B$^2$ are independently cap structure; W$^1$ and W$^2$ are independently a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, —NR$^1$— (where R$^1$ is an alkyl group having 1 to 6 carbon atoms), a benzene ring, a heteroaromatic ring, a saturated or partially unsaturated hydrocarbon ring and a saturated or partially unsaturated hetero ring; here, at least either one of B$^1$ or B$^2$ is substituted with —W$^3$—R$^2$ (where W$^3$ is a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, —NR$^1$— (where R$^1$ is an alkyl group having 1 to 6 carbon atoms), a benzene ring, a heteroaromatic ring, a saturated or partially unsaturated hydrocarbon ring and a saturated or partially unsaturated hetero ring; R$^2$ is a functional group being capable of reacting with silica or a functional group being capable of reacting with a carbon-carbon unsaturated bond); B$^1$ and B$^2$ may be substituted with the same or different 1 to 4 groups independently selected from the group consisting of halogen, alkyl and alkoxy; hydrogen atoms in a secondary ammonium (—N$^+$H$_2$—) moiety may be substituted with alkyl, alkylcarbonyl, alkylaminocarbonyl, alkoxycarbonyl, optionally-substituted phenylcarbonyl, optionally-substituted phenylaminocabonyl, or optionally-substituted phenoxycarbonyl; when a plurality of R$^1$, R$^2$ and W$^3$ exists, those may be the same or different.

B$^1$ and B$^2$ are the same or different, and are preferably 3,5-di-tert-butylphenyl, 3,5-dimethylphenyl, 2,6-dimethylphenyl, 3,5-dinitrophenyl, 4-tert-butylphenyl, 2,4,6-trimethylphenyl, tert-butyl, diphenylmethyl, trityl, naphthyl and anthracenyl, more preferably 3,5-di-tert-butylphenyl, 3,5-dimethylphenyl, 4-tert-butylphenyl, 2,4,6-trimethylphenyl, tert-butyl and diphenylmethyl.

Each of W$^1$, W$^2$ and W$^3$ is the same or different, and is preferably a single bond, or a spacer being composed of 1 to 100 atoms and having a constituent unit selected from the group consisting of linear or branched alkylene chain, —CO—O—, —O—CO—, —O—, —CO—, —S—, —NH—, a benzene ring, a 5-membered or 6-membered nitrogen-containing heteroaromatic ring, a 5-membered or 6-membered saturated or partially unsaturated hydrocarbon ring and a 5-membered or 6-membered saturated or partially unsaturated nitrogen-containing hetero ring; and more preferably a spacer being composed of 1 to 80 atoms and having a constituent unit selected from the group consisting of a linear alkylene chain, —CO—O—, —O—CO—, —O—, —S—, a benzene ring and a 5-membered or 6-membered saturated or partially unsaturated nitrogen-containing hetero ring.

Preferred as a group which may be substituted for B$^1$ and B$^2$ are halogen, alkyl having 1 to 6 carbon atoms and alkoxy having 1 to 6 carbon atoms; more preferred are fluorine and methyl.

Preferred as a group which may be substituted for hydrogen atoms of the secondary ammonium (—N$^+$H$_2$—) moiety$^2$ are alkyl having 1 to 6 carbon atoms, alkylcarbonyl having 1 to 6 carbon atoms, alkylaminocarbonyl having 1 to 6 carbon atoms, alkoxycarbonyl having 1 to 6 carbon atoms, phenylcarbonyl which may be substituted with 1 to 3 methyl groups or halogen, phenylaminocarbonyl which may be substituted with 1 to 3 methyl groups or halogen and phenoxycarbonyl which may be substituted with 1 to 3 methyl groups or halogen; more preferred are alkyl having 1 to 6 carbon atoms, alkylcarbonyl having 1 to 6 carbon atoms, alkylaminocarbonyl having 1 to 6 carbon atoms, alkoxycarbonyl having 1 to 6 carbon atoms and phenylaminocarbonyl which may be substituted with 1 to 3 methyl groups or halogen; further preferred are phenylaminocarbonyl which may be substituted with 1 to 3 methyl groups or halogen.

Functional groups which are capable of reacting with silica are preferably alkoxysilyl, acetoxysilyl and chlorosilyl; more preferably alkoxysilyl.

Functional groups which are capable of reacting with the carbon-carbon unsaturated bond are preferably nitrile oxide, azide, nitron, nitrileimine, sydnone, methylol phenol, mercapto, (poly)sulfide, vinyl, vinylene, ethynyl, ethynylene, cyano, isocyanate, isocyanurate, epoxy, glycidyloxy, acryloyl, methacryloyl and ureido; more preferably nitrile oxide, azide, mercapto, (poly)sulfide, epoxy and glycidyloxy; further preferably nitrile oxide, mercapto and (poly)sulfide.

When the cyclic molecule is substituted with functional group being capable of reacting with silica, the axial molecule is substituted with functional group being capable of reacting with the carbon-carbon unsaturated bond. In other words, when the above-mentioned $R^3$ is a functional group being capable of reacting with silica, the above-mentioned $R^2$ is a functional group being capable of reacting with the carbon-carbon unsaturated bond.

On the other hand, when the cyclic molecule is substituted with functional group being capable of reacting with the carbon-carbon unsaturated bond, the axial molecule is substituted with functional group being capable of reacting with silica. In other words, when the above-mentioned $R^3$ is a functional group being capable of reacting with the carbon-carbon unsaturated bond, the above-mentioned $R^2$ is a functional group being capable of reacting with silica.

(Rotaxane Compound)

One suitable mode of the rotaxane compound according to the embodiment of the present invention is a compound represented by the following formula (2):

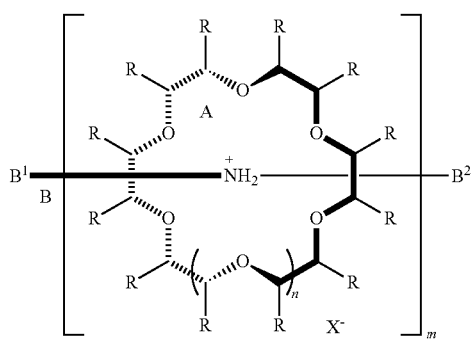

(2)

wherein the ring A is a crown ether cyclic molecule, in which 1 to 3 of ring-forming oxygen atoms may be replaced by NH or S; each of the Rs is independently a hydrogen atom, or a substituent or a reactive group which may be bonded via a spacer; the two Rs attaching to adjacent carbon atoms together with the carbon atoms bonded to the Rs may form an aromatic ring (preferably a benzene ring), a heteroaromatic ring, a saturated or partially unsaturated hydrocarbon ring or a saturated or partially unsaturated hetero ring; "n" is an integer of 2 to 9 (preferably an integer of 2 to 5); "m" is 1 or a repeating number of 2 or more; the axial molecule B has "m" secondary ammonium (—$N^+H_2$—) moieties; $B^1$ and $B^2$ are independently cap structure; and $X^-$ is a counter anion of the secondary ammonium salt.

Examples of the counter anion represented by $X^-$ include a perchloric acid ion, a trifluoromethane sulfonic acid ion, a hexafluoro phosphoric acid ion, a trifluoroacetic acid ion, a tetrafluoroboric acid ion and the like.

Examples of the above-mentioned substituent include alkylthio, mercapto, aminomethyl, amino, hydroxyl, hydroxymethyl, carboxyl, carboxymethyl, halogen, alkoxy, alkoxycarbonylamino (carbamate), carbamoyl, vinyl, allyl, ethynyl, formyl, acrylate, methacrylate, ether and the like. Examples of the ethers include polyethers which may have one or more substituents selected from the group consisting of phenyl and oxo, etc.

The above-mentioned spacer is capable of having one or more constituent unit selected from the group consisting of a linear or branched alkylene chain, —CO—O—, —O—CO—, —O—, —CO—, —S—, —CS—, —NH—, —$NR^1$— (where $R^1$ is a substituent such as an alkyl group), an aromatic ring, a heteroaromatic ring, a saturated or partially unsaturated hydrocarbon ring, a saturated or partially unsaturated hetero ring and the like.

Further, compounds obtained by converting one or more of the secondary ammonium (—$N^+H_2$—) moieties of the compound represented by the formula (2) to tertiary ammonium, amide, urea, carbamate or the like are raised as a preferred mode.

More suitable one mode of the rotaxane compound according to the embodiment of the present invention is a rotaxane compound represented by the following formula (2a), (2b) or (2c), in which one axial molecule penetrates through one crown ether cyclic molecule:

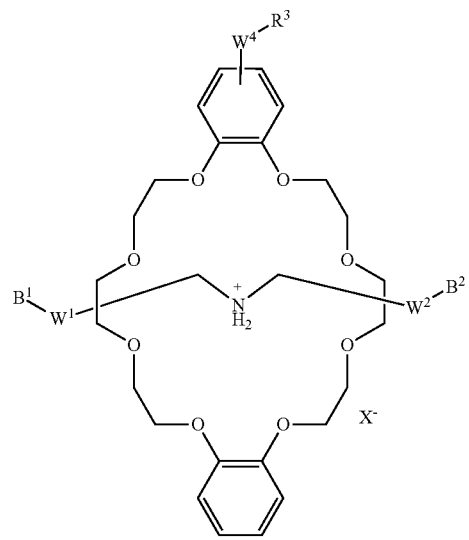

(2a)

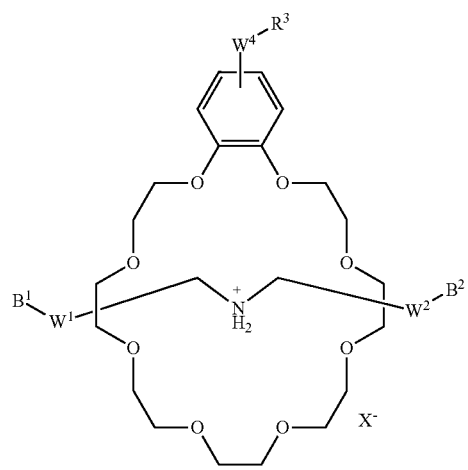

(2b)

-continued (2c)

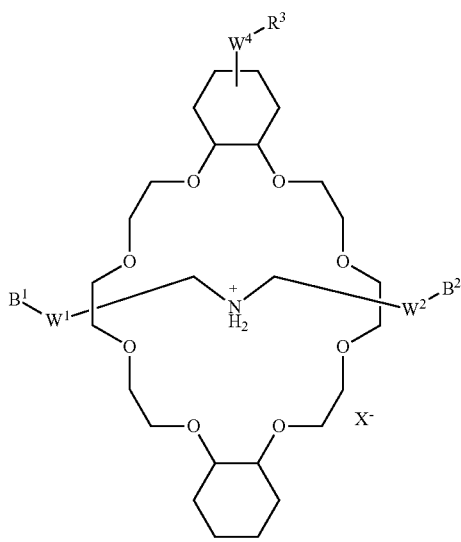

wherein $B^1$, $B^2$, $W^1$, $W^2$, $W^3$, $W^4$, $R^1$, $R^2$, $R^3$ and $X^-$ are the same as those defined above; here, the crown ether cyclic molecule may be substituted with the same or different 1 to 4 groups independently selected from the group consisting of halogen, alkyl and alkoxy; 1 to 3 of ring-forming oxygen atoms may be replaced by NH or S; $B^1$ and $B^2$ may be substituted with the same or different 1 to 4 groups independently selected from the group consisting of halogen, alkyl and alkoxy; hydrogen atoms in the secondary ammonium (—$N^+H_2$—) moiety may be substituted with alkyl, alkylcarbonyl, alkylaminocarbonyl, alkoxycarbonyl, optionally-substituted phenylcarbonyl, optionally-substituted phenylaminocabonyl, or optionally-substituted phenoxycarbonyl; when a plurality of $R^1$, $R^2$ and $W^3$ exists, those may be the same or different. When the hydrogen atoms in the secondary ammonium (—$N^+H_2$—) moiety have been replaced by substituents, no counter anion represented by $X^-$ exists.

When the cyclic molecule is substituted with functional group being capable of reacting with silica, the axial molecule is substituted with functional group being capable of reacting with the carbon-carbon unsaturated bond. In other words, when the above-mentioned $R^3$ is a functional group being capable of reacting with silica, the above-mentioned $R^2$ is a functional group being capable of reacting with the carbon-carbon unsaturated bond.

On the other hand, when the cyclic molecule is substituted with functional group being capable of reacting with the carbon-carbon unsaturated bond, the axial molecule is substituted with functional group being capable of reacting with silica. In other words, when the above-mentioned $R^3$ is a functional group being capable of reacting with the carbon-carbon unsaturated bond, the above-mentioned $R^2$ is a functional group being capable of reacting with silica.

(Method of Preparing a Rotaxane Compound)

The rotaxane compound according to the embodiment of the present invention can be prepared by a known method such as a Threading-Capping method, a method described in a reference document (e.g., Oleo Science, Vol. 5, No. 5, 2005, p. 209), or a method according thereto.

Nitrile oxide which is a functional group being capable of reacting with a carbon-carbon unsaturated bond can be introduced easily, for example, by allowing phenyl isocyanate or the like to act, in the presence of a base, on a nitroalkane compound synthesized in accordance with a known method. Further, the functional group being capable of reacting with the carbon-carbon unsaturated bond other than nitrile oxide according to the embodiment of the present invention can also be introduced in accordance with a known method.

A mercapto group and a (poly)sulfide group, which are functional groups being capable of reacting with the carbon-carbon unsaturated bond, can be introduced, for example, by using an alkenyl group introduced in the cyclic molecule or the axial molecule as a starting point. Specifically, a mercapto group and a (poly)sulfide group can be introduced in the cyclic molecule or the axial molecule, for example, by adding alkylthiol or alkyldithiol to an alkenyl group introduced in the cyclic molecule or the axial molecule.

Various silyl groups such as alkoxysilyl which are functional groups being capable of reacting with silica can be introduced, for example, by using, as a starting point, an alkenyl group introduced in the cyclic molecule or the axial molecule. Specifically, various silyl groups can be introduced in the cyclic molecule or the axial molecule, for example, by 1,3-dipolar cycloaddition of a nitrile oxide compound having various silyl groups to the alkenyl group introduced in the cyclic molecule or the axial molecule.

The rotaxane compound according to the embodiment of the present invention and an intermediate thereof can be subjected to isolation and refining by means of refining methods usually used in an organic synthesis chemistry, for example, neutralization, filtration, extraction, rinsing, drying, condensing, recrystallization, various kinds of chromatography and the like. Further, each intermediate can be subjected to a subsequent reaction particularly without specifically refining.

An optically active substance of the rotaxane compound according to the embodiment of the present invention can be prepared by using an optically active starting material or its intermediate or subjecting a racemic body being a final product to optical resolution. Examples of the optical resolution method include a physical separation method using an optically activating column and a chemical separation method such as a fractional crystallization method. A diastereomer which is the rotaxane compound according to the embodiment of the present invention can be prepared by, for example, a fractional crystallization method.

<Polymer Composition>

The polymer composition can be prepared by using the rotaxane compound according to the embodiment of the present invention as a silane coupling agent. By blending the rotaxane compound to the polymer composition, enhancement of elasticity, stress relaxation and abrasion resistance can be expected. In addition, loss tangent (tan δ) and complex modulus of a vulcanized rubber composition can be measured with a commercially available viscoelastic spectrometer. Tensile properties of a vulcanized rubber and a thermoplastic rubber can be measured in accordance with JIS K 6251. A stress relaxation test of a vulcanized rubber can be performed in accordance with JIS K 6263.

Non-limited examples of applications of the polymer composition include a material for tires, an optical material, a medical material, a biomaterial, contact lens, a coating agent and an adhesive; and an environment-related material, daily commodities, materials for civil engineering and construction, battery-related materials, foods, health products, sports goods and materials thereof, cloth and fashion materials, fibers, toys and entertainment materials, art-related materials, car-related materials and the like.

A polymer having an unsaturated bond can be used suitably as the polymer which the polymer composition according to the embodiment of the present invention comprises. The polymer having an unsaturated bond is not limited particularly as long as it is a polymer having reactive multi-bonds which can be subjected to an addition reaction by a 1,3-dipolar cycloaddition reaction, a radical addition reaction, an electrophilic addition reaction, a nucleophilic addition reaction or the like. Examples of the polymer include an acrylonitrile-butadiene copolymer, polyisoprene, a styrene-butadiene copolymer, polybutadiene, polychloroprene, an ethylene-propylene-diene copolymer, a styrene-butadiene-styrene block copolymer, a styrene-isoprene-styrene block copolymer and the like.

Examples of the polymer being a rubber compound include a PAN (polyacrylonitrile) compound which is a compound having a nitrile group (C≡N) in its molecule; a diene compound which is a compound having a carbon-carbon double bond (C=C); an EPDM (ethylene-propylene-diene copolymer rubber) compound; a polynorbornene compound; an NBR (nitrile rubber) compound which is a compound having a nitrile group and a carbon-carbon double bond in its molecule; and the like.

Examples of the diene rubber include isoprene rubbers including a natural rubber (NR) and a polyisoprene rubber (IR), a butadiene rubber (BR), a styrene-butadiene copolymer rubber (SBR), a styrene-isoprene-butadiene copolymer rubber (SIBR), a chloroprene rubber (CR) and the like.

When the rubber component comprises the NR, a content thereof is within a range of, for example, 1 to 100% by mass, 5 to 95% by mass, 10 to 90% by mass, 1 to 20% by mass, 5 to 30% by mass, 10 to 40% by mass, 20 to 50% by mass, 30 to 60% by mass, 40 to 70% by mass, 50 to 80% by mass, 60 to 90% by mass, 70 to 100% by mass or 80 to 100% by mass.

When the rubber component comprises the BR, a content thereof is within a range of, for example, 1 to 100% by mass, 5 to 95% by mass, 10 to 90% by mass, 1 to 20% by mass, 5 to 30% by mass, 10 to 40% by mass, 20 to 50% by mass, 30 to 60% by mass, 40 to 70% by mass, 50 to 80% by mass, 60 to 90% by mass, 70 to 100% by mass or 80 to 100% by mass.

When the rubber component comprises the SBR, a content thereof is within a range of, for example, 1 to 100% by mass, 5 to 95% by mass, 10 to 90% by mass, 1 to 20% by mass, 5 to 30% by mass, 10 to 40% by mass, 20 to 50% by mass, 30 to 60% by mass, 40 to 70% by mass, 50 to 80% by mass, 60 to 90% by mass, 70 to 100% by mass or 80 to 100% by mass.

Examples of applications of the rubber include a tire, a hose, a belt, a packing, a coating film of an electric wire, an anti-vibration rubber, a rubber for construction, a roller, a footgear, sealing parts, a medical material, car-related parts, daily commodities, sports goods, batteries and the like.

When the polymer is a water-soluble polymer, examples thereof include starch, gelatin, carboxymethyl cellulose, methyl cellulose, polyamine, polyvinyl alcohol, polyacrylic acid, polyacrylamide, polyethylene oxide, polyvinyl pyrrolidone, polyvinylamide, polypeptide and the like.

Examples of applications of the water-soluble polymer include medicines, a medical material, cosmetics, toiletry goods, foods, coatings, adhesives, ink, water treatment such as waste water treatment for civil engineering and construction, electronics, batteries and the like.

An amount of the rotaxane compound according to the embodiment of the present invention is within a range of, for example, 0.01 to 20 parts by weight, 0.01 to 10 parts by weight, 0.05 to 10 parts by weight, 0.05 to 5 parts by weight, 0.1 to 10 parts by weight or 0.2 to 5 parts by weight based on 100 parts by weight of the polymer having an unsaturated bond.

Silica is suitably used as a filler compounded in the polymer composition according to the embodiment of the present invention. Silica is not limited particularly, and silica prepared by a dry method (anhydrous silica), silica prepared by a wet method (hydrous silica) or the like can be used. Among these, hydrous silica prepared by the wet method is preferable because it has many silanol groups. Silica may be used alone, or may be used in combination of two or more thereof.

When the rubber composition comprises a silica, the content thereof is t within a range of, for example, 1 to 150 parts by mass, 5 to 130 parts by mass, 10 to 100 parts by mass, 5 to 50 parts by mass, or 30 to 80 parts by mass based on 100 parts by mass of the rubber component.

Further, fillers other than silica may be used. Such fillers are not limited particularly, and, examples thereof include carbon black, aluminum hydroxide, alumina (aluminum oxide), calcium carbonate, talc, clay and the like. From the viewpoint of reinforceability, carbon black is suitably used. These fillers may be used alone or may be used in combination of two or more thereof.

Carbon black commonly used for rubbers can be used appropriately. Specifically N110, N115, N120, N125, N134, N135, N219, N220, N231, N234, N293, N299, N326, N330, N339, N343, N347, N351, N356, N358, N375, N539, N550, N582, N630, N642, N650, N660, N683, N754, N762, N765, N772, N774, N787, N907, N908, N990, N991 and the like can be used suitably. Besides those mentioned above, carbon black synthesized by Sumitomo Rubber Industries, Ltd. can also be used suitably.

When the rubber composition comprises a carbon black, the content thereof is within a range of, for example, 1 to 150 parts by mass, 5 to 130 parts by mass, 10 to 100 parts by mass, 5 to 50 parts by mass, or 30 to 80 parts by mass based on 100 parts by mass of the rubber component.

The content of the whole fillers is within a range of, for example, 1 to 200 parts by mass, 5 to 150 parts by mass, 10 to 100 parts by mass, 5 to 50 parts by mass, or 30 to 80 parts by mass based on 100 parts by mass of the rubber component.

When the polymer composition according to the embodiment of the present invention is a rubber composition for tires, in addition to the above-mentioned polymers and fillers, compounding agents and additives which have been used in a tire industry, for example, wax, oil, anti-oxidant, stearic acid, zinc oxide, a vulcanizing agent, a vulcanization accelerator and the like can be compounded appropriately if necessary.

When the rubber composition comprises wax, the content thereof is within a range of, for example, 0.5 to 10 parts by mass, 0.5 to 5 parts by mass, or 1 to 3 parts by mass based on 100 parts by mass of the rubber component.

When the rubber composition comprises oil, the content thereof is within a range of, for example, 5 to 100 parts by mass, 10 to 70 parts by mass, or 10 to 50 parts by mass based on 100 parts by mass of the rubber component.

The anti-oxidant is not limited particularly, and those having been used in a field of rubbers can be used. Examples thereof include quinoline-, quinone-, phenol- and phenylenediamine-based anti-oxidants and the like.

When the rubber composition comprises the anti-oxidant, the content thereof is within a range of, for example, 0.5 to 10 parts by mass, 0.5 to 5 parts by mass, or 1 to 3 parts by mass based on 100 parts by mass of the rubber component.

When the rubber composition comprises stearic acid, the content thereof is within a range of, for example, 0.2 to 10 parts by mass, 0.5 to 5 parts by mass, or 1 to 3 parts by mass based on 100 parts by mass of the rubber component.

When the rubber composition comprises zinc oxide, the content thereof is within a range of, for example, 0.5 to 10 parts by mass, 0.5 to 5 parts by mass, or 1 to 3 parts by mass based on 100 parts by mass of the rubber component.

Sulfur is suitably used as the vulcanizing agent. Examples of usable sulfur include powdered sulfur, oil-treated sulfur, precipitated sulfur, colloidal sulfur, insoluble sulfur, highly dispersible sulfur and the like.

When the rubber composition comprises sulfur as the vulcanizing agent, the content thereof is within a range of, for example, 0.5 to 3.0 parts by mass, 1.0 to 2.5 parts by mass, or 0.5 to 2.0 parts by mass based on 100 parts by mass of the rubber component.

Examples of a vulcanization accelerator include sulfenamide-, thiazole-, thiuram-, thiourea-, guanidine-, dithiocarbamate-, aldehyde amine- or aldehyde ammonia-, imidazoline- and xanthate-based vulcanization accelerators. These vulcanization accelerators may be used alone or may be used in combination of two or more thereof. Among these, sulfenamide-based vulcanization accelerators, thiazole-based vulcanization accelerators and guanidine-based vulcanization accelerators are preferred, and sulfenamide-based vulcanization accelerators are preferred more. Further, a combination use of sulfenamide-based vulcanization accelerator and other vulcanization accelerators (preferably thiazole-based vulcanization accelerator and/or guanidine-based vulcanization accelerator) can be raised as a preferred mode.

Examples of the sulfenamide-based vulcanization accelerators include N-tert-butyl-2-benzothiazolylsulfenamide (TBBS), N-cyclohexyl-2-benzothiazolylsulfenamide (CBS), N,N-dicyclohexylbenzothiazole-2-sulfenamide (DCBS) and the like. Among these, N-tert-butyl-2-benzothiazolylsulfenamide (TBBS) and N-cyclohexyl-2-benzothiazolylsulfenamide (CBS) are preferred.

Examples of the thiazole-based vulcanization accelerator include 2-mercaptobenzothiazole, cyclohexylamine salt of 2-mercaptobenzothiazole, di-2-benzothiazolyl disulfide and the like. Among these, 2-mercaptobenzothiazole is preferable.

Examples of the guanidine-based vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine is preferable.

When the rubber composition comprises the vulcanization accelerator, the content thereof is, for example, within a range of 0.1 to 5 parts by mass, 0.5 to 3 parts by mass, or 0.5 to 2 parts by mass based on 100 parts by mass of the rubber component.

The polymer composition according to the embodiment of the present invention can be prepared by a known method. For example, when the polymer composition is a rubber composition, it can be prepared by kneading each of the above-mentioned components with a rubber kneader such as an open roll, a Banbury mixer, or a closed kneader and then vulcanizing a resultant kneaded product. Exemplified hereinbelow is a method of preparing a rubber composition. Chemicals (including a rotaxane compound) except sulfur and vulcanization accelerators are kneaded with a Banbury mixer to obtain a kneaded product. Subsequently sulfur and vulcanization accelerators are added to the obtained kneaded product, and a mixture is kneaded with an open roll to obtain an un-vulcanized rubber composition. Further, the obtained un-vulcanized rubber composition is subjected to press vulcanization to obtain a vulcanized rubber composition.

EXAMPLE

The present invention is then explained by means of Examples, but is not limited to the Examples.

Meanings of symbols and abbreviations in Examples are shown below.

DIC: Diisopropylcarbodiimide
$Bu_3P$: Tri(tert-butyl)phosphine
THF: Tetrahydrofuran
Ph: Phenyl
Et: Ethyl Example 1

A rotaxane compound (1-4) was synthesized by a method and conditions shown by means of the following formulation.

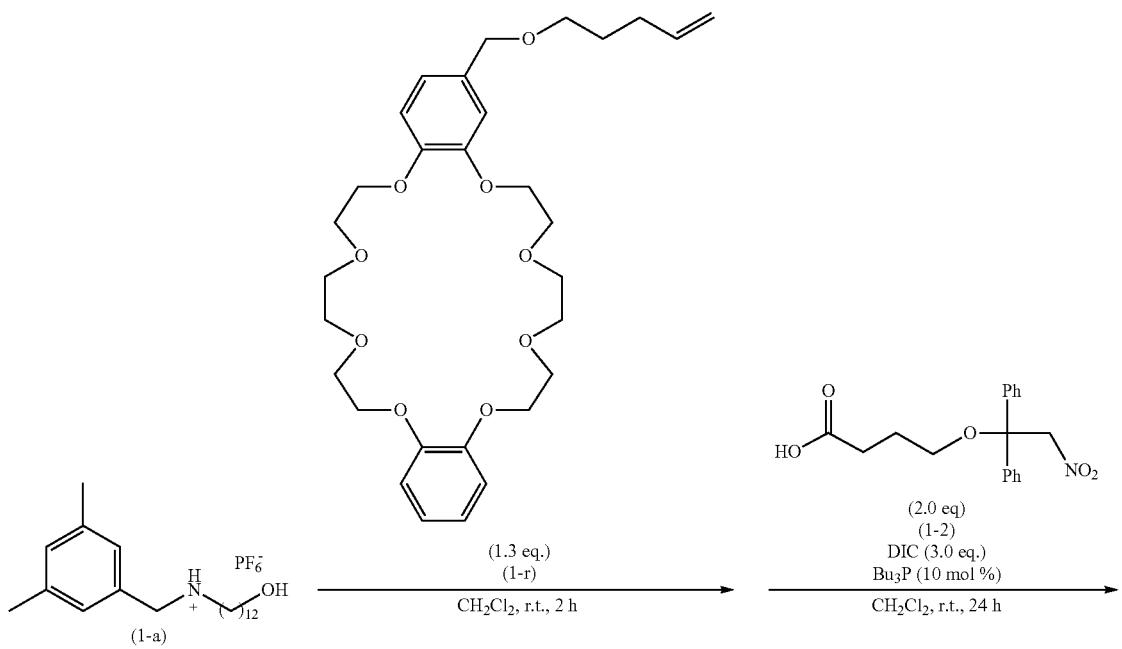

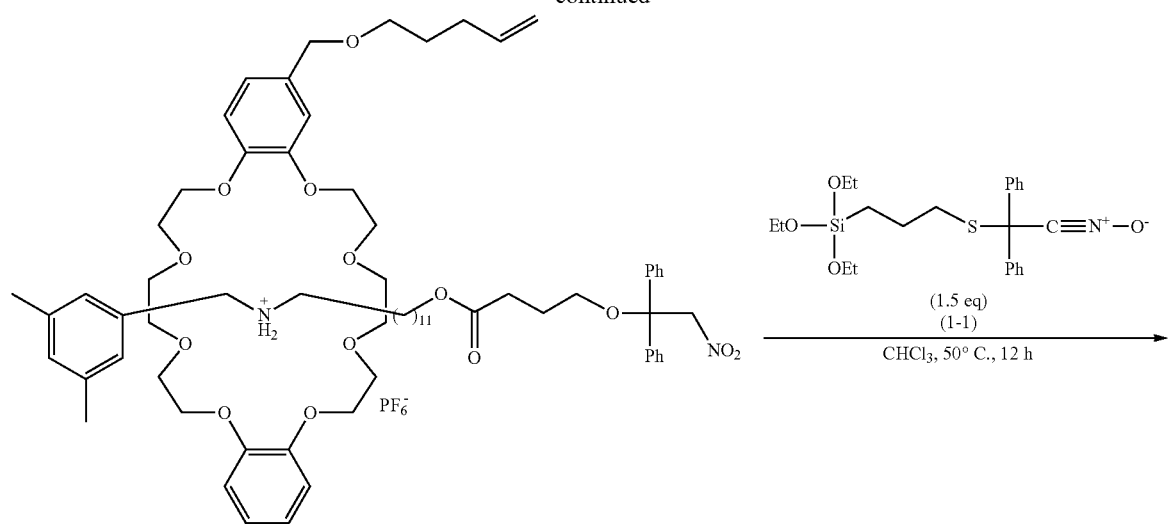
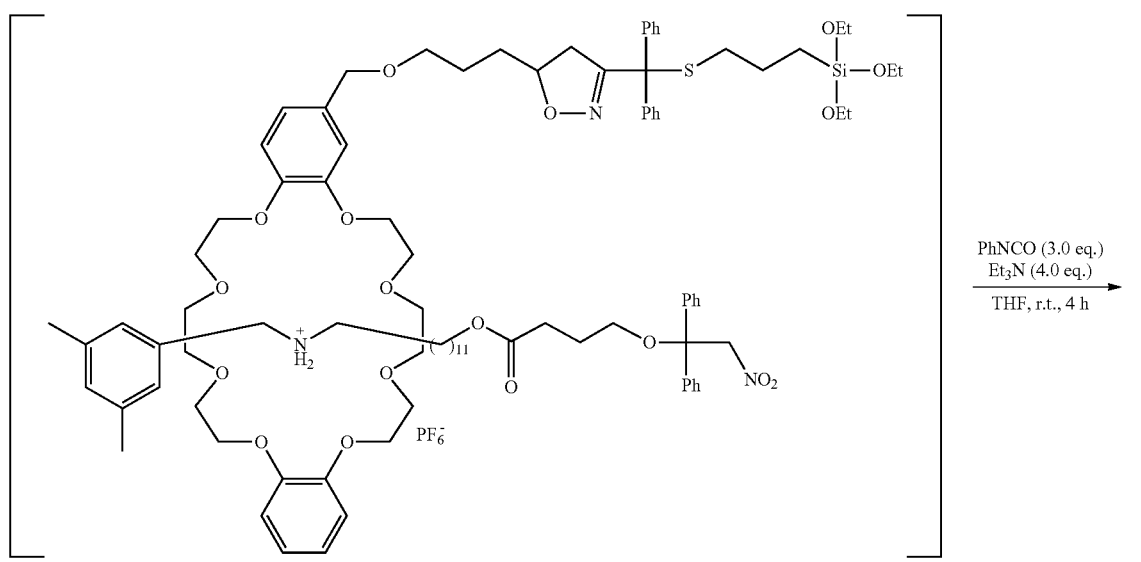
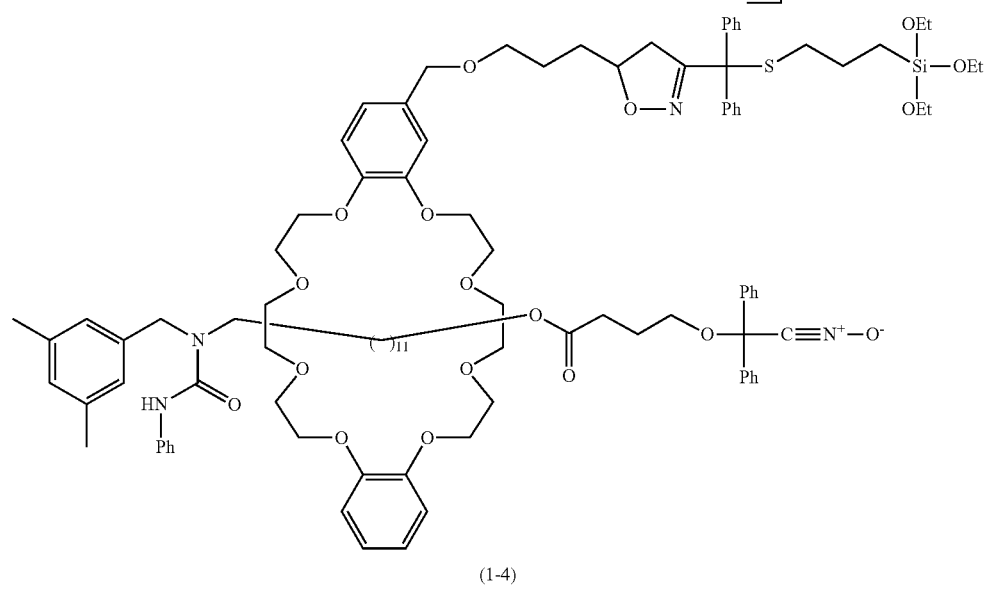

Example 1-1: Synthesis of Alkoxysilane Compound (1-1)

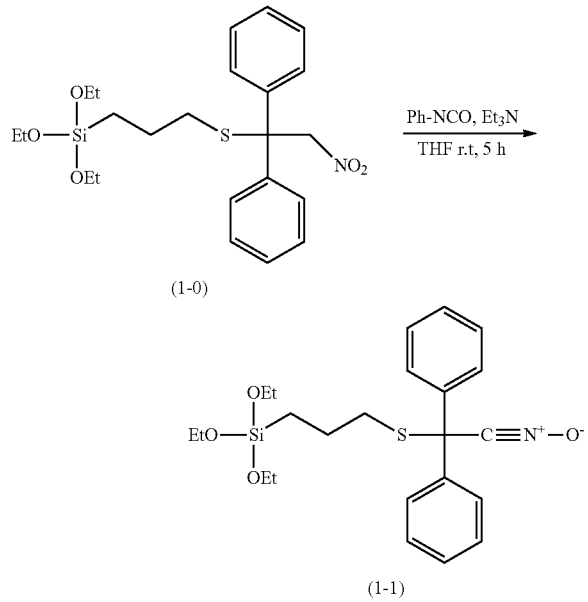

A nitroalkane compound (1-0) was obtained in accordance with a known method using commercially available 3-mercaptopropyltriethoxysilane and diphenylnitroethene. Phenyl isocyanate (6.3 g) and triethylamine (7.8 g) were added to a THF (150 ml) solution of the compound (1-0) (12 g), followed by 5-hour stirring at room temperature. After filtration of a reaction solution, a solvent of a filtrate was distilled off, followed by refining using silica gel column chromatography (eluent: ethyl acetate/hexane=1/10). Thus, an alkoxysilane compound (1-1) (10 g) was obtained.

$^1$H-NMR (500 Hz, CDCl$_3$, 298K): δ (ppm) 7.60-7.47 (m, 4H), 7.42-7.30 (m, 6H), 3.78 (q, J=7.0 Hz, 6H), 2.61 (t, J=7.3 Hz, 2H), 1.72-1.65 (m, 2H), 1.20 (t, J=7.0 Hz, 9H), 0.70-0.67 (m, 2H);

$^{13}$C-NMR (125 Hz, CDCl$_3$, 298K): δ (ppm) 139.2, 128.8, 128.6, 127.4, 58.4, 57.2, 35.7, 22.0, 18.3, 10.3;

IR (NaCl): υ 2287 (CNO) cm$^{-1}$;

MALDI-TOF MS (Matrix: dithranol, Cationizing agent: CF$_3$COONa): m/z calcd for C$_{23}$H$_{31}$NO$_4$SSiNa [M+Na]$^+$: 468.17, found: 468.34.

Example 1-2: Synthesis of Nitroalkane Compound (1-3)

An axial molecule component (1-a) (470 mg) was added to a dichloromethane (1.4 mL) solution of a cyclic molecule component (1-r) (710 mg), followed by 2-hour stirring. Subsequently thereto were added a compound (1-2) (660 mg), DIC (0.47 mL) and (tert-butyl)phosphine (50 μL), followed by 24-hour stirring at room temperature. A reaction solution was subjected to re-precipitation in hexane and refining using GPC for isolation (eluent: chloroform) to obtain a nitroalkane compound (1-3) (620 mg).

$^1$H-NMR (500 Hz, CDCl$_3$, 298K): δ (ppm) 7.35-7.21 (m, 20H), 7.19-7.05 (m, 2H), 6.97-6.82 (m, 10H), 5.85-5.77 (m, 1H), 5.34 (s, 2H), 5.04-4.94 (m, 2H), 4.51 (q, J=7.0 Hz, 2H), 4.40 (s, 2H), 4.25-4.21 (m, 4H), 4.12-4.09 (m 4H), 4.05 (t, J=6.9 Hz, 2H), 3.86-3.81 (m 8H), 3.64-3.61 (m, 4H), 3.46 (m, t, J=6.9 Hz, 2H), 3.43-3.38 (m, 4H), 3.09-3.03 (m, 2H), 2.49 (t, J=7.5 Hz, 2H), 2.13 (q, J=7.2 Hz, 2H), 1.98-1.93 (m, 2H), 1.73-1.67 (m, 2H), 1.64-1.58 (m, 2H), 1.44-0.96 (m, 20H);

$^{13}$C-NMR (125 Hz, CDCl$_3$, 298K): δ (ppm) 173.6, 147.5, 147.4, 146.9, 141.4, 138.3, 138.2, 132.3, 132.3, 130.7, 128.4, 128.1, 127.3, 126.6, 121.8, 121.0, 114.8, 112.7, 112.6, 112.4, 112.1, 81.3, 79.7, 72.4, 70.7, 70.2, 69.7, 68.4, 68.3, 68.2, 64.5, 62.0, 52.2, 49.0, 31.1, 30.4, 29.5, 29.4, 29.3, 29.2, 28.9, 28.6, 26.6, 26.4, 25.9, 25.0, 21.2;

MALDI-TOF MS (Matrix: dithranol, Cationizing agent: CF$_3$COONa): m/z calcd for C$_{69}$H$_{97}$N$_2$O$_{14}$Na [M+Na]$^+$: 1177.74, found: 1177.26.

Example 1-3: Synthesis of Rotaxane Compound (1-4)

The compound (1-1) (290 mg) was added to a chloroform (5.0 mL) solution of the compound (1-3) (560 mg), followed by 12-hour stirring at 50° C. The solvent was distilled off, the compound was dissolved in THF (8.6 mL), and thereto were added phenyl isocyanate (290 mg) and triethylamine (350 mg), followed by 4-hour stirring at room temperature. After filtration of a reaction solution, a solvent of a filtrate was distilled off, followed by refining using GPC for isolation (eluent: chloroform) to obtain a rotaxane compound (1-4) (200 mg).

$^1$H-NMR (500 Hz, CDCl$_3$, 298K): δ (ppm) 7.52-7.14 (m, 23H), 6.92-6.67 (m, 12H), 4.58-4.52 (m, 1H), 4.48 (s, 2H), 4.36 (s, 2H), 4.20-4.04 (m, 8H), 4.00 (t, J=6.9 Hz, 2H), 3.74 (q, J=6.7 Hz, 6H), 3.73-3.68 (m, 8H), 3.61-3.36 (m, 14H), 2.96-2.91 (m, 1H), 2.53-2.48 (m, 3H), 2.33-2.24 (m, 2H), 2.20 (s, 6H), 2.15-2.09 (m, 2H), 2.00-1.95 (m, 2H), 1.74-1.65 (m, 1H), 1.59-1.50 (m, 8H), 1.18 (t, J=6.7 Hz, 9H), 1.30-0.91 (m, 18H), 0.62-0.59 (m 2H);

$^{13}$C-NMR (125 Hz, CDCl$_3$, 298K): δ (ppm) 173.7, 161.0, 155.8, 148.2, 147.7, 141.3, 141.2, 140.7, 140.6, 139.2, 137.4, 130.5, 128.9, 128.6, 128.5, 128.4, 128.3, 128.1, 127.3, 126.6, 126.3, 124.9, 121.7, 120.5, 119.9, 119.8, 111.9, 111.5, 83.9, 80.9, 72.7, 70.8, 69.7, 69.5, 68.4, 68.3, 68.2, 65.9, 64.8, 61.0, 58.3, 49.2, 47.5, 41.6, 33.8, 31.8, 30.8, 30.1, 29.8, 29.7, 29.6, 29.3, 28.6, 27.6, 26.6, 25.9, 25.8, 24.7, 22.1, 21.4, 18.3, 10.4;

IR (NaCl): υ 2275 (CNO) cm$^{-1}$;

MALDI-TOF MS (Matrix: dithranol, Cationizing agent: CF$_3$COONa): m/z calcd for C$_{99}$H$_{130}$N$_4$O$_{18}$SSiNa [M+Na]$^+$: 1745.93, found: 1745.89.

INDUSTRIAL APPLICABILITY

The rotaxane compound of the present invention can be used as a silane coupling agent imparting specific dynamic characteristic and physical properties to a composition obtained by compounding the rotaxane compound thereto.

The invention claimed is:
1. A rotaxane compound comprising:
  one or more cyclic molecules and an axial molecule penetrating through inner holes of the cyclic molecules and having cap structures disposed lest the cyclic molecules should be detached,
  wherein:
    one of the cyclic molecule or the axial molecule has one of a functional group being capable of reacting with silica or a functional group being capable of reacting with a carbon-carbon unsaturated bond, and the other one of the cyclic molecule or the axial molecule has the other one of the functional group being capable of reacting with silica or the functional group being capable of reacting with a carbon-carbon unsaturated bond, the cyclic molecule is a crown ether cyclic molecule represented by the following formula (1a), (1b), or (1c):

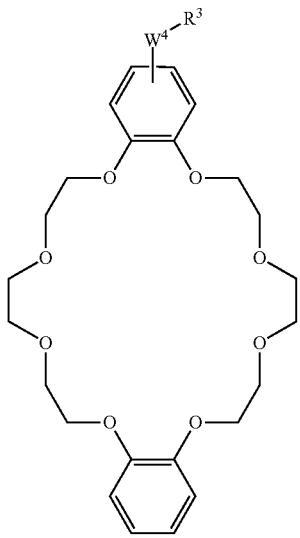

(1a)

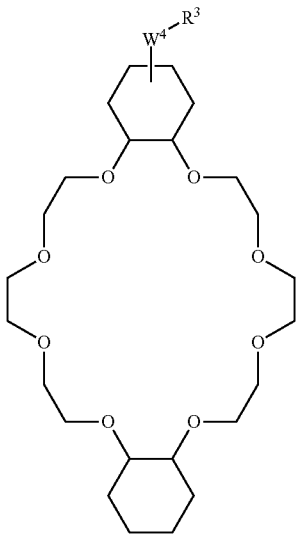

(1c)

wherein:

$W^4$ is a single bond, or a spacer composed of 1 to 100 atoms and having one or more constituent units selected from the group consisting of linear or branched alkylene chain, —CO—O—, —O—CO—, —O—, —CO—, —S—, —CS—, —NH— and —NR$^1$—, where R$^1$ is an alkyl group having 1 to 6 carbon atoms, a benzene ring, a heteroaromatic ring, a saturated or partially unsaturated hydrocarbon ring, or a saturated or partially unsaturated hetero ring;

$R^3$ is a functional group capable of reacting with silica or a functional group being capable of reacting with a carbon-carbon unsaturated bond;

the crown ether represented by formula (1a), (1b), or (1c) may be substituted with the same or different 1 to 4 groups independently selected from the group consisting of halogen, alkyl, and alkoxy; and 1 to 3 of oxygen atoms constituting the ring may be replaced by NH or S, and if there are plural cyclic molecules in the rotaxane compound, the cyclic molecules may be the same or different;

the axial molecule is an axial molecule represented by the following formula (3):

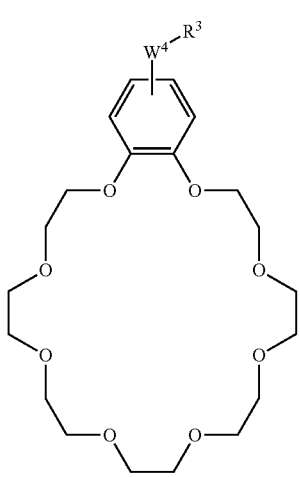

(1b)

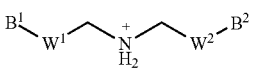

(3)

wherein:

$B^1$ and $B^2$ are independently a cap structure having an outer diameter larger than an inner diameter of the cyclic molecule, wherein at least one of B1 and B2 is selected from the group consisting of phenyl, tert-butyl, diphenylmethyl, trityl, naphthyl, and anthracenyl;

$W^1$ and $W^2$ are independently a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, and —NR$^1$— where R$^1$ is an alkyl group having 1 to 6 carbon atoms, a benzene ring, a heteroaromatic ring, a saturated or partially unsaturated hydrocarbon ring, or a saturated or partially unsaturated hetero ring;

at least either one of $B^1$ or $B^2$ is substituted with —$W^3$—$R^2$, where:

$W^3$ is a single bond, or a spacer being composed of 1 to 100 atoms and having one or more constituent unit selected from the group consisting of linear or branched alkylene chain, —CO—O—, —O—CO—, —O—, —CO—, —S—, —CS—, —NH—, and —NR$^1$—, where $R^1$ is an alkyl group having 1 to 6 carbon atoms, a benzene ring, a heteroaromatic ring, a saturated or partially unsaturated hydrocarbon ring, or a saturated or partially unsaturated hetero ring;

$R^2$ is the functional group being capable of reacting with silica or the functional group being capable of reacting with a carbon-carbon unsaturated bond;

$B^1$ and $B^2$ may be substituted with the same or different 1 to 4 groups independently selected from the group consisting of halogen, alkyl, and alkoxy;

hydrogen atoms in the secondary ammonium —$N^+H_2$— moiety of formula (3) may be substituted with alkyl, alkylcarbonyl, alkylaminocarbonyl, alkoxycarbonyl, optionally-substituted phenylcarbonyl, optionally-substituted phenylaminocabonyl, or optionally-substituted phenoxycarbonyl; and when a plurality of $R^1$, $R^2$ and $W^3$ exists, those may be the same or different, the functional group being capable of reacting with a carbon-carbon unsaturated bond is at least one selected from the group consisting of nitrile oxide, azide, nitron, nitrileimine, sydnone, methylolphenol, mercapto, sulfide, vinyl, vinylene, ethynyl, ethynylene, cyano, isocyanate, isocyanurate, epoxy, glycidyloxy, acryloyl, methacryloyl and ureido, and the functional group being capable of reacting with silica is at least one selected from the group consisting of alkoxysilyl, acetoxysilyl and chlorosilyl.

2. The rotaxane compound of claim 1, wherein one of the axial molecules penetrates one of the cyclic molecules.

3. A polymer composition comprising a polymer having a carbon-carbon unsaturated bond and the rotaxane compound of claim 1.

4. The polymer composition of claim 3, wherein the polymer is a diene rubber.

5. A rubber composition comprising a diene rubber, silica and the rotaxane compound of claim 1.

6. The rotaxane compound of claim 1, wherein the alkoxysilyl is trimethoxysilyl, triethoxysilyl, triisopropoxysilyl, dimethoxymethylsilyl, diethoxymethylsilyl, dimethylmethoxysilyl or dimethylethoxysilyl.

* * * * *